United States Patent
Foody

(10) Patent No.: US 9,505,668 B2
(45) Date of Patent: Nov. 29, 2016

(54) PROCESS FOR PRODUCING A FUEL AND BYPRODUCT FROM BIOMASS OR BIOMASS DERIVED MATERIAL

(71) Applicant: Iogen Corporation, Ottawa (CA)

(72) Inventor: Patrick J. Foody, Ottawa (CA)

(73) Assignee: Iogen Corporation, Ottawa (CA)

( * ) Notice: Subject to any disclaimer, the term of this patent is extended or adjusted under 35 U.S.C. 154(b) by 0 days.

(21) Appl. No.: 14/700,700

(22) Filed: Apr. 30, 2015

(65) Prior Publication Data

US 2015/0315502 A1    Nov. 5, 2015

Related U.S. Application Data

(60) Provisional application No. 61/987,111, filed on May 1, 2014.

(51) Int. Cl.

| | | |
|---|---|---|
| C07C 27/00 | (2006.01) | |
| C07C 1/04 | (2006.01) | |
| C10L 1/04 | (2006.01) | |
| C10L 1/02 | (2006.01) | |
| C10J 3/82 | (2006.01) | |
| C07C 37/68 | (2006.01) | |
| G06Q 30/02 | (2012.01) | |
| C07C 37/00 | (2006.01) | |
| C07C 37/72 | (2006.01) | |
| C07C 37/74 | (2006.01) | |
| C10G 2/00 | (2006.01) | |

(52) U.S. Cl.
CPC ............... *C07C 1/04* (2013.01); *C07C 1/045* (2013.01); *C07C 37/004* (2013.01); *C07C 37/68* (2013.01); *C07C 37/72* (2013.01); *C07C 37/74* (2013.01); *C10G 2/32* (2013.01); *C10J 3/82* (2013.01); *C10L 1/02* (2013.01); *C10L 1/04* (2013.01); *G06Q 30/02* (2013.01); *G06Q 30/0207* (2013.01); *C10J 2300/0906* (2013.01); *C10J 2300/0916* (2013.01); *C10J 2300/0959* (2013.01); *C10J 2300/1618* (2013.01); *C10J 2300/1846* (2013.01); *C10L 2200/0469* (2013.01); *C10L 2200/0492* (2013.01); *C10L 2290/04* (2013.01); *C10L 2290/42* (2013.01); *Y02E 50/32* (2013.01)

(58) Field of Classification Search
CPC .. C07C 37/68; C07C 1/04; C10J 2300/1687; C10J 2300/1846; C10J 2300/0916; C10J 2300/0906; C10J 2300/1618; C10L 2200/0469; C10L 2200/0492; C10L 2290/04; C10L 2290/42
USPC ........................................ 518/700; 48/197 R
See application file for complete search history.

(56) References Cited

U.S. PATENT DOCUMENTS

| | | | |
|---|---|---|---|
| 2,113,951 A | 4/1938 | Shuman | |
| 2,334,691 A | 11/1943 | Andersen | |
| 4,193,776 A | 3/1980 | Wasala et al. | |
| 4,605,790 A | 8/1986 | Wojtkowski | |
| 5,171,895 A | 12/1992 | Brient | |
| 5,750,009 A | 5/1998 | Duncan et al. | |
| 7,674,443 B1* | 3/2010 | Davis ................. | C01B 17/0404 423/210 |
| 8,217,210 B2 | 7/2012 | Agrawal et al. | |
| 8,217,211 B2 | 7/2012 | Agrawal et al. | |
| 8,673,031 B2 | 3/2014 | Dale et al. | |
| 8,685,685 B2 | 4/2014 | Retsina et al. | |
| 2009/0165378 A1 | 7/2009 | Agblevor | |
| 2009/0217575 A1 | 9/2009 | Raman et al. | |
| 2010/0083575 A1 | 4/2010 | Varadaraj et al. | |
| 2011/0067991 A1 | 3/2011 | Hornung et al. | |
| 2011/0124748 A1* | 5/2011 | Kuku ........................ | C10L 1/02 518/700 |
| 2011/0232164 A1* | 9/2011 | Siskin .................... | C10B 57/045 44/307 |
| 2012/0090221 A1* | 4/2012 | Banasiak ................ | C10B 49/10 44/300 |
| 2012/0240456 A1 | 9/2012 | Ida et al. | |
| 2013/0058856 A1* | 3/2013 | Yuan ........................ | B01J 21/04 423/245.1 |
| 2013/0144087 A1 | 6/2013 | Arora | |
| 2013/0232853 A1 | 9/2013 | Peterson et al. | |
| 2013/0295628 A1 | 11/2013 | Retsina et al. | |

FOREIGN PATENT DOCUMENTS

| | | |
|---|---|---|
| CA | 2834052 A1 | 11/2012 |
| EP | 1352042 B1 | 10/2003 |
| WO | 2009048875 A2 | 4/2009 |

(Continued)

OTHER PUBLICATIONS

Bain et al., "Biomass Gasification", NREL, Presentation at USDA Thermochemical Conversion Workshop, Pacific Northwest National Laboratory, Richland, WA, Sep. 6, 2006.

Baliban et al., "Toward Novel Hybrid Biomass, Coal, and Natural Gas Processes for Satisfying Current Transportation Fuel Demands, 1: Process Alternatives, Gasification Modeling, Process Simulation, and Economic Analysis", Industrial & Engineering Chemistry Research, vol. 49, No, 16 (2010) 7343-7370.

Brage et al., "Separation of Phenols and Aromatic Hydrocarbons from Biomass Tar Using Aminopropylsilane Normal-Phase Liquid Chromatography", Journal of Chromatography, vol. 538 (1991) 303-310.

Ciolkosz, "Manufacturing Fuel Pellets from Biomass", PennState College of Agricultural Sciences, Renewable and Alternative Energy Fact Sheet, 2009.

(Continued)

*Primary Examiner* — Jafar Parsa
(74) *Attorney, Agent, or Firm* — Knobbe Martens Olson & Bear LLP

(57) ABSTRACT

The present invention provides a process for producing a fuel and a byproduct from biomass or biomass derived material. The invention comprises providing a processed biomass feedstock and carrying out or causing one or more parties to subject the processed biomass feedstock to gasification to produce carbon monoxide and hydrogen and cresylic acid and recovering the cresylic acid or a portion thereof. The processed biomass feedstock may be co-gasified with coal. The hydrogen from the gasification may be recovered or the carbon monoxide and hydrogen may be further reacted to produce a fuel or fuel intermediate. One or more products obtained from the process are provided, for use as, or to produce a transportation or heating fuel. The invention may allow for advantaged fuel credit generation.

21 Claims, No Drawings

(56) References Cited

FOREIGN PATENT DOCUMENTS

| WO | 2010134077 A2 | 11/2010 |
|---|---|---|
| WO | 2011028543 A2 | 3/2011 |
| WO | 2012090369 A1 | 7/2012 |
| WO | 2012106801 A1 | 8/2012 |
| WO | 2013089928 A1 | 6/2013 |
| WO | 2013134754 A1 | 9/2013 |

OTHER PUBLICATIONS

ComPAKco et al., "Phase I Biomass Enhanced Refined Lignite Demonstration Project", ComPAKco and Great American Energy Contract No. R005-0012, Sep. 15, 2010.

Dakota Gasification Company, "Dephenolized Cresylic Acid", Dakota Gasification Company Website, Access Date Jan. 6, 2014.

Devi et al. "A Review of the Primary Measures for Tar Elimination in Biomass Gasification Processes", Biomass and Bioenergy, vol. 24 (2003) 125-140.

Etiegni et al., "Physical and Chemical Characteristics of Wood Ash", Bioresource Technology, Vo. 37 (1991) 173-178.

Fjellerup et al., "Formation, Decomposition and Cracking of Biomass Tars in Gasification", Technical University of Denmark report, Department of Mechanical Engineering Biomass Gasification Group, ISBN nr,: 87-7475-326-6, Apr. 2005.

Guo et al., "Catalytic Effects of NaOH and Na2CO3 Additives on Alkali Lignin Pyrolysis and Gasification", Applied Energy, vol. 95 (2012) 22-30.

Haimiao et al., "Characteristics of Tar Formation During Cellulose Hemicellulose and Lignin Gasification", Fuel vol. 118 (2014) 250-256.

Han et al., "The Reduction and Control Technology of Tar During Biomass Gasification/Pyrolysis: An Overview", Renewable and Sustainable Energy Reviews, vol. 12 (2008) 397-416.

Kirubakaran et al., "A Review on Gasification of Biomass", Renewable and Sustainable Energy Reviews, vol. 13 (2009) 179-186.

Kopyscinski et al., "Production of Synthetic Natural Gas (SNG) from Coal and Dry Biomass—A Technology Review from 1950 to 2009", Fuel, vol. 89 (2010) 1763-1783.

Kruse et al., "Biomass Gasification in Supercritical Water: Influence of the Dry Matter Content and the Formation of Phenols", Industrial & Engineering Chemistry Research, vol. 42, No. 16, (2003) 3711-3717.

Kruse, "Hydrothermal Biomass Gasification", Journal of Supercritical Fluids, vol. 47 (2009) 391-399.

Kumar, "Pyrolysis and Gasification of Lignin and Effect of Alkali Addition", a Thesis, Georgia Institute of Technology, Aug. 2009.

Lopamudra et al,, "A Review of the Primary Measures for Tar Elimination in Biomass Gasification Processes", Biomass and Bioenergy, vol. 24 (2003) 125-140.

Matsumura et al., "Biomass Gasification in Near- and Super-Critical Water: Status and Prospects", Biomass and Bioenergy, vol. 29 (2005) 269-292.

Matsumura et al., "Supercritical Water Treatment of Biomass for Energy and Material Recovery", Combustion Science and Technology, vol. 178 (2006) 509-536.

McKendry, "Energy Production from Biomass (part 1): Overview of Biomass" Bioresource Technology, vol. 83 (2002) 37-46.

McKendry, "Energy Production from Biomass (part 2): Conversion Technologies", Bioresource Technology 83 (2002) 47-54.

McKendry, "Energy Production from Biomass (part 3): Gasification Technologies", Bioresource Technology 83 (2002) 55-63.

Merisol Ltd., "Cresylic Acid" Product Stewardship Summary, Jun. 30, 2009.

Milne et al., "Biomass Gasifier Tars—Their Nature, Formation and Conversion", National Renewable Energy Laboratory, NREL/TP-570-25357, Nov. 1998.

Mitchell et al., "Torrefaction?What's that?", USDA Forest Service, Fueling the Future: 2010 Council on Forest Engineering Annual Meeting, Auburn, Alabama, Jun. 6-9, 2010.

Morey, "Biomass Densification" University of Minnesota, Biomass Conversion to Heat & Electricity Workshop, Heartland Community College, Normal, IL, Mar. 11, 2009.

Muangrat et al., "Alkali-Promoted Hydrothermal Gasification of Biomass Food Processing Waste: A Parametric Study", International Journal of Hydrogen Energy, vol. 35 (2010) 7405-7415.

Obernberger et al., "Concentrations of Inorganic Elements in Biomass Fuels and Recovery in the Different Ash Fractions", Biomass and Bioenergy, vol. 12, No. 3 (1997) 211-224.

Olanders et al., "Characterization of Ashes From Wood and Straw" Biomass and Bioenergy, vol. 8, No. 2 (1995) 105-115.

Pinto et al., "Effect of Experimental Conditions on Co-Gasification of Coal, Biomass and Plastics Wastes with Air/ Steam Mixtures in a Fluidized Bed System", Fuel, vol. 82 (2003) 1967-1976.

Rabou et al., "Tar in Biomass Producer Gas, the Energy Research Centre of the Netherlands (ECN) Experience: An Enduring Challenge", Energy Fuels, vol. 23 (2009) 6189-6198.

Raveendran et al., "Influence of Mineral Matter on Biomass Pyrolysis Characteristics", Fuel, vol. 74, No. 12 (1995) 1812-1822.

Sami et al., "Co-Firing of Coal and Biomass Fuel Blends", Process in Energy and Combustion Science, vol. 27 (2001) 171-214.

Schmieder et al., "Hydrothermal Gasification of Biomass and Organic Waste", Journal of Supercritical Fluids, vol. 17 (2000)145-153.

Sevilla, "The Production of Carbon Materials by Hydrothermal Carbonization of Cellulose", Carbon, vol. 47 (2009) 2281-2289.

Stiller et al., "Co-Processing of Agricultural and Biomass Waste with Coal" Fuel Processing Technology, vol. 49, No. 1-3 (1996) 167-175.

Teng et al., "Thermogravimetric Studies on the Kinetics of Rice Hull Pyrolysis and the Influence of Water Treatment", Industrial & Engineering Chemistry Research, vol. 37 (1998) 3806-3811.

Tumuluru et al., "A Review on Biomass Classification and Composition, Co-firing Issues and Pretreatment Methods", Idaho National Laboratory, ASABE Presentation, Aug. 2011.

Turna, "Sasol Lurgi Fixed Bed Dry Bottom Gasification for Fuels and Chemicals", Sasol-Lurgi Technology Company (Pty) Ltd, Presentation at 2nd International Freiberg Conference on IGCC & XtL Technologies, Freiburg, Germany, May 8-12, 2007.

U.S. DOE, "Practical Experience Gained During the First Twenty Years of Operation of the Great Plains Gasification Plant and Implications for Future Projects", U.S. Department of Energy, Apr. 2006.

Van Dyk et al. "A Diamond in the Global World of Carbon", Sasol Technology R&D Coal and Gas Processing, a Presentation, 2012.

Van Dyk et al., "Suitability of Feedstocks for the Sasol-Lurgi Fixed Bed Dry Bottom Gasification Process" Sasol Technology Gasification Technologies 2001, San Francisco CA, Oct. 7-10, 2001.

Wahyudiono et al., "Decomposition of Lignin Alkaline and Chemicals Recovery in Sub- and Supercritical Water", Kumamoto University, 2004.

Wild et al., "Biomass Valorisation by Staged Degasification. A New Pyrolysis-Based Thermochemical Conversion Option to Produce Value-Added Chemicals from Lignocellulosic Biomass", Journal of Analytical and Applied Pyrolysis, vol. 85 (2009) 124-133.

Wu et al., "Pyrolysis/Gasification of Cellulose, Hemicellulose and Lignin for Hydrogen Production in the Presence of Various Nickel-Based Catalysts", Fuel, vol. 106 (2013) 697-706.

Zimmerman et al., "Potential of Reed Canary Grass as a Biofuel in Michigan's Eastern Upper Peninsula", Government of Michigan (2009), 6 pages.

Zwart et al., "Tar Removal From Low-Temperature Gasifiers", ERA-NET Bioenergy, ECN-E—10-008, Apr. 2010.

Zwart, "Allothermal Gasification of Biomass into Chemicals and Secondary Energy Carriers", Energy Research Centre of the Netherlands, Presented at International Conference on Polygeneration Strategies (ICPS09) in Wien, Austria, Sep. 1-4, 2009.

\* cited by examiner

PROCESS FOR PRODUCING A FUEL AND BYPRODUCT FROM BIOMASS OR BIOMASS DERIVED MATERIAL

INCORPORATION BY REFERENCE TO PRIORITY APPLICATION

This application claims benefit of U.S. Provisional Application No. 61/987,111, filed May 1, 2014, which is incorporated herein by reference in its entirety.

FIELD

The present invention relates to a process for producing a fuel and a byproduct from biomass or biomass derived material.

BACKGROUND

Much effort has been applied in recent years to the production of fuels and chemicals from biomass and biomass derived material due to their low cost and wide availability. Often agricultural and forestry residues are burned or landfilled. Thus using these materials for fuel production offers an attractive alternative to their disposal. Further, the use of biomass and biomass derived material to make fuels provides reductions in GHG emissions relative to fossil fuels. The extraction of coal or crude oil for use in industry results in the release of carbon into the atmosphere that was previously stored in the earth, and thereby has a net effect of increasing the levels of atmospheric $CO_2$. By contrast, $CO_2$ released from utilizing biomass is relatively benign, given that it simply returns to the atmosphere carbon that was previously removed therefrom by plant photosynthesis.

While the production of transportation or heating fuel from biomass or biomass derived material has received significant attention in recent years, there are also developing opportunities for making other products from these materials. The production of co-products with fuels can allow for reductions in the net production cost of biofuels and can diversify revenue sources from fuel production operations.

One potential co-product of fuel production from biomass is cresylic acid. Cresylic acid is a chemical product that can have significant commercial value. Cresylic acid comprises ortho-cresol (o-cresol), meta-cresol (m-cresol) and/or para-cresol (p-cresol) and has many industrial uses. Mixed cresols can be used as disinfectants, preservatives and wire enamel solvents, o-cresol finds use as a solvent, disinfectant and chemical intermediate, m-cresol can be used to produce herbicides, insecticides, antioxidants and explosives, while p-cresol is used in the formulation of antioxidants and in the fragrance and dye industries. Cresylic acid is typically produced from coal or oil.

Despite the advantages of using biomass or biomass derived material, coal and crude oil are still the predominant feedstocks in use today to make chemicals or fuels. While biomass is known to have the potential to reduce greenhouse gas (GHG) emissions from the fossil fuel industry, its use as a starting material for producing fuels has proven to be difficult in practice due to economic and technical challenges. There is thus a need in the art to overcome some of the challenges of making biomass derived fuels at lower net cost. The generation of co-products from fuel production can offer such benefit.

SUMMARY

The present invention relates generally to a means to make biofuels via gasification processes that produce syngas. According to one aspect of the invention, there is provided a process by which cresylic acid is produced by using a processed biomass feedstock that is co-gasified with coal as part of a gasification process to produce syngas, which is subsequently used to make a fuel. Cresylic acid can subsequently be recovered and provided for use in various industrial applications.

Co-gasifying a biomass feedstock with coal provides numerous advantages over operating a gasification plant in which such biomass is used exclusively as the starting material. Gasifying biomass feedstock with coal can reduce GHG emissions associated with a fuel or fuel intermediate obtained from the syngas, such as methane. This in turn can allow for advantaged fuel credit generation, thereby providing a mechanism for incentivizing commercialization of technologies for converting biomass material to transportation or heating fuels. A further advantage of co-gasifying is that the composition of the feed to the gasification can be varied by adjusting the ratio of coal and biomass feedstock. This provides a methodology for controlling the average feedstock composition introduced to the gasification, and according to certain embodiments, could potentially be utilized as a mechanism to increase tar production, which in turn could result in improvements in cresylic acid production. Additionally, co-gasifying biomass material with coal can enable effective gasification by permitting a tailored tar production, including the production of cresylic acid.

In a further aspect of the invention, a biomass or a biomass derived material is processed in a manner to improve its gasification properties. The processed biomass feedstock is provided or supplied to a gasification plant in a form suitable for gasification. The biomass may be prepared for gasification by mechanical treatment, releasing extractives, densification or any combination of these methods, as described further herein.

In one example of the invention, the process comprises treating biomass or biomass derived material in one or more processing steps to remove certain components present in the biomass or biomass derived material that can interfere with the gasification. This in turn may improve the economics of biomass gasification and cresylic acid recovery. For example, biomass or biomass derived material comprises alkali salts that can be problematic in gasification. Their presence during gasification can lead to a mobile phase of incombustible residue, known as slag or "clinker", which can result in equipment blockage in gasifiers that employ dry ash removal. As discussed herein, this problem is particularly pronounced with potassium salts that are often present at high levels in biomass feedstocks. Accordingly, in certain embodiments, the present invention allows for reductions in slag, thereby improving the economics of gasifying biomass and recovering cresylic acid.

Moreover, subjecting the biomass or biomass derived material to one or more processing steps to release extractives can produce a processed biomass feedstock having improvements in its net calorific value, also referred to as a "lower heating value" as measured in British Thermal Units per pound ("Btu/lb") by ISO 1928:2009—Determination of gross calorific value by the bomb calorimetric method and calculation of net calorific value (incorporated herein by reference). Thus, in further embodiments, the biomass or biomass derived material is subjected to one or more processing steps involving releasing extractives to produce a processed biomass feedstock having a higher net calorific value as measured in Btu/lb than could otherwise be attained in the absence of such processing step(s).

According to further embodiments of the invention, a processed biomass feedstock that is densified is provided to gasification to reduce the amount of fines or other particles present in the gasification. Since fines and other small particles can disrupt gasification, operating with reduced levels of fines can improve the gasification operation. In certain gasification reactors, a bed should be formed that is permeable so that the gas can flow between the feedstock. However, the presence of fines in the reactor can interfere with or prevent the flow of gas therethrough. Thus, by removing or reducing the build-up of such fines, densification can serve to reduce disruptions in gas flow through the bed that would otherwise occur. Yet another potential advantage of densification is that it can result in a densified feedstock having a higher energy content per unit volume ("Btu/ft$^3$").

The present invention will be described with regard to further embodiments. However, it will be apparent to persons skilled in the art that a number of variations and modifications can be made without departing from the scope of the invention as defined in the claims.

DETAILED DESCRIPTION OF THE PREFERRED EMBODIMENT

Biomass or Biomass Derived Material

The material subjected to gasification or co-gasification is a processed biomass feedstock. The processed biomass feedstock is obtained from biomass or any material that has been obtained directly or indirectly from plant biomass, referred to herein as "biomass derived material". Examples of biomass and biomass derived material are provided below.

The combined content of cellulose, hemicellulose and lignin in biomass is greater than 25 wt % (w/w). In an embodiment of the invention, the biomass comprises 5 to 30 wt % (w/w) lignin. Sucrose, fructose and starch can be present in the biomass, but usually in lesser amounts than cellulose and hemicellulose.

The biomass derived material may contain at least 20 wt %, at least 30 wt %, at least 50 wt %, at least 60 wt % or at least 70 wt % lignin. The biomass derived material may or may not contain cellulose, depending on whether or not it has been removed in prior processing steps. In an embodiment of the invention, the amount of cellulose in the biomass derived material is from 0 to 50 wt % (w/w).

Examples of biomass and biomass derived material include (i) energy crops; (ii) residues, byproducts or waste from the processing of plant material in a facility, or feedstock derived therefrom; (iii) agricultural residues; (iv) forestry material; (v) material derived from pulp and paper processing; (vi) pulp and paper residues; and (vii) municipal waste or components removed from municipal waste.

Energy crops include biomass crops such as grasses, including C4 grasses, such as switch grass, energy cane, sorghum, cord grass, rye grass, *miscanthus*, reed canary grass, C3 grasses such as *Arundo donax* or a combination thereof.

Residues, byproducts or waste from the processing of plant material in a facility or feedstock derived therefrom include residues remaining after obtaining sugar from plant biomass such as sugar cane bagasse, sugar cane tops and/or leaves, beet pulp, or residues remaining after removing sugar from Jerusalem artichoke or residues remaining after grain processing, such as corn fiber, corn stover or bran from grains. Agricultural residues include, but are not limited to soybean stover, corn stover, rice straw, sugar cane tops and/or leaves, rice hulls, barley straw, corn cobs, wheat straw, canola straw, oat straw, oat hulls, or corn cobs.

Forestry material includes any species of hardwood or softwood. The term includes residues, byproducts, waste or non-waste material from processing any hardwood or softwood species. Examples of waste include residues from sawmills, trimmings or slash from logging operations. Pulp and paper residue, includes non-pulp and non-paper products from chemical pulping or paper making such as black liquor, spent sulfite liquor, sludge, broke, fines or precipitated lignin.

Municipal waste includes post-consumer material or waste from a variety of sources, such as domestic, commercial, institutional and industrial sources. For example, the term includes refuse from waste collection and sewage sludge.

Biomass or biomass derived material can be a mixture of fibers that originate from different kinds of plant material, including mixtures of cellulosic and non-cellulosic biomass. In addition, the biomass may comprise fresh biomass, partially dried biomass, fully dried biomass, or a combination thereof. Moreover, new biomass varieties may be produced from any of those listed above by plant breeding or by genetic engineering.

In an embodiment of the invention, the biomass or biomass derived material is a non-woody material such as (i) an energy crop, (ii) residues, byproducts or waste from the processing of plant biomass or feedstock derived therefrom in a facility, or (iii) agricultural residues. In another embodiment of the invention, the biomass or biomass derived material is straw, stover or an energy crop. As used herein, straw refers to the stem, stalk and/or foliage portion of crops remaining after the removal of starch and/or sugar containing components for consumption. Examples of straw include, but are not limited to sugar cane tops and/or leaves, oat straw, wheat straw, rye straw, oat straw, rice straw and barley straw. Stover includes the stalk and foliage portion of crops after the removal of starch and/or sugar containing components of plant material for consumption. Examples of stover include, but are not limited to soybean stover, sorghum stover and corn stover.

Non-woody biomass generally contains higher levels of ash than woody biomass. Such non-woody biomass will contain greater than 0.5 wt % ash (w/w), greater than 1 wt % ash (w/w), or more typically greater than 3 wt % (w/w) ash. The ash includes, but is not limited to, silica, and salts of potassium, calcium and sodium. These elements can be measured by atomic absorption. In certain embodiments of the invention, the ash content of the non-woody biomass is between about 0.5 wt % and about 18 wt %, between about 1 wt % and about 17 wt %, between about 2 wt % and about 17 wt %, between about 3 wt % and about 17 wt % or between about 3.5 wt % and about 16 wt % (w/w). The amount of ash is expressed as the percentage of residue remaining after dry oxidation at 575° C. in accordance with NREL Technical Report NREL/TP-510-42622, January 2008, which is incorporated herein by reference. The results are reported relative to a 105° C. oven dried sample (dried overnight).

In an embodiment of the invention, the biomass is woody plant material, which includes material from any hardwood or softwood species. Woody biomass includes stems, trunks, branches or a combination thereof from trees. Woody biomass can be provided from tree removal operations to remove unwanted trees such as forest management harvesting, branches and undersized trees from timber harvesting, sawmill waste or trees from forests or plantations dedicated to fuel production.

Processed Biomass Feedstock

By the term "processed biomass feedstock", it is meant any type of woody or non-woody plant biomass or biomass derived material that has been processed to any degree to make it suitable for gasification to produce syngas.

The processed biomass feedstock may contain at least 20 wt %, at least 30 wt %, at least 50%, at least 60% or at least 70% (w/w) lignin. The processed biomass feedstock may or may not contain cellulose, depending on whether or not it has been removed during the processing.

Processing of biomass or biomass derived material includes treatments selected from mechanical, thermal, biological or chemical treatment, densification and one or more combinations thereof. The biomass or biomass derived material may be processed (i) by mechanical treatment, such as by particle size reduction, including chipping and/or by classification; (ii) to remove extractives, for example soluble ash and/or hemicellulose; (iii) by densification; or (iv) any combination of these processing steps, so as to improve its handleability or gasification properties relative to its native form.

(a) Mechanical Treatment

The mechanical treatment includes size reduction and/or classification. Examples of mechanical treatment to reduce the size of the biomass or biomass derived material include, but are not limited to, chipping, refining, milling, grinding, agitation, shredding, compression/expansion, or other types of mechanical action. According to the invention, the size reduction process produces a processed biomass feedstock comprising feedstock particles of a certain size. The processed biomass feedstock most advantageously has a particle size such that at least 90% of the particles by weight are ¼ inches to 6 inches, ¼ inches to 5 inches, ¼ inches to 4 inches or ½ inch to 3 inches in diameter. The size distribution is measured by passing the solids through a sieve having round openings of a defined diameter. It should be appreciated that the biomass or biomass derived material need not be subjected to size reduction if the particle size of the feedstock is already of a suitable particle size, such as between ¼ to 6 inches.

Size reduction by mechanical action can be performed by any type of equipment adapted for the purpose, for example, but not limited to, chippers, hammer mills, grinders, tub-grinders, roll presses, refiners, shredders and hydrapulpers. If size reduction is performed, it can be performed while the biomass or biomass derived material is dry or moist, i.e., having a moisture content of 0% to 60%, or while water is added to the biomass. Dry shredding can be carried out, for example, with a shredder, hammer mill or tub grinder, while wet shredding may be performed with pulpers.

If the biomass is a woody material, chips may be produced from whole pulp logs that have been debarked or from residual wood that is a byproduct of a sawmill. Chips may be produced by disk chippers or drum chippers.

The mechanical treatment may additionally or alternatively comprise classification of biomass or biomass derived material. Classification of biomass or biomass derived material involves any methodology for separating material by size and/or grade. Separating biomass or biomass derived material by size and/or grade can be carried out by disks, screens or magnets to remove metals. The screens can be oscillating, vibrating or rotating. Classification of biomass or biomass derived material and particle size reduction can be carried out together or as separate operations.

After mechanical treatment, the processed biomass feedstock can be fed directly to gasification, or subjected to further processing as set out below. An example of a processed biomass feedstock that can be fed directly to gasification is chips.

(b) Releasing Extractives

The process of the invention may comprise treating biomass or biomass derived material so as to release extractives. By "extractive releasing process step" it is meant a liquid processing step involving contacting the biomass or any biomass derived material with a solution to remove one or more extractives so that they become part of the soluble component of a liquid medium. The biomass derived material from which extractives are released may result from one or more prior processing steps of biomass, including heat treatment, mechanical processing, addition of one or more chemicals or catalysts, or combinations thereof. Extractives may also be released from a biomass that has not been subjected to one or more prior processing steps.

Without being limiting in any manner, the biomass or biomass derived material may be slurried prior to or during the step of releasing extractives. In a further embodiment, the biomass or biomass derived material is not slurried but rather contacted with liquid with or without any feedstock size reduction.

If slurrying is conducted, it may be carried out in any batch or continuous mixing vessel at any desired consistency. In an embodiment of the invention, the undissolved solids content is between about 1 and about 50 wt % (w/w) or between about 1 and about 30 wt % (w/w). The undissolved solids content is a weight ratio of dry solids to liquid in a process stream, or other solution, and is arrived at by determining the weight of a sample and then filtering the sample through filter paper and washing with water to isolate the undissolved solids. The isolated, undissolved solids are dried overnight at 105° C., in a drying dish, and then weighed. The undissolved solids content is quantified by determining, as a percent, the number of grams of dry solids per gram of process stream or other solution.

In an embodiment of the invention, at least about 5 wt %, about 10 wt % or about 15 wt % (w/w) of insoluble components remain as a solids component after processing steps to release extractives as measured by dry weight. In a further embodiment, between about 5 wt % and about 90 wt %, or between about 10 wt % and about 80 wt %, or between 40 wt % and 80 wt %, or between about 10 wt % and 50 wt %, or between 10 wt % and 60 wt % or between 10 wt % and 40 wt % (w/w) of extractives are removed as measured by weight of the original biomass.

Extractives include components that become part of a liquid medium after processing steps that include application of heat, mechanical energy, chemicals, catalysts or a combination thereof. The catalysts may be chemical or biological. Examples of extractives include oil, sugar, inorganic salt, organic acid, organic salt, byproducts of the process, such as degradation products and fermentation byproducts, protein, soluble lignin, pectin, or a combination thereof. The liquid medium can be an aqueous solution, an organic solvent, an ionic liquid, or a combination thereof.

The sugar includes sugar monomers, oligomers comprising two or more sugar monomers, sugar polymers and combinations thereof. Examples of sugars include hemicellulose, polymers or oligomers of six carbon sugars, polymers or oligomers of five carbon sugars and monomers of six and five carbon sugars.

Examples of inorganic salt include potassium, calcium and sodium salts. Other salts that may be removed are magnesium, manganese and iron. The salts may be present as sulfate salts, phosphate salts, chloride salts, bromide salts, glycolate salts, trifluoro acetate salts or oxylate salts. The level of inorganic salt removed may be 0.5 wt % to 10 wt % or 1 wt % to 8 wt % (w/w) as measured by weight of the biomass prior to the one or more processing steps. The level of inorganic salt in the biomass is determined as a wt % (w/w) and compared to the inorganic salt in the processed biomass feedstock as a wt % (w/w). Determination of the amount of inorganic salt in the biomass before and after processing and the percent removed involves measuring residue remaining after dry oxidation as set out above in connection with ash determination before and after the one or more processing steps to remove extractives.

In an embodiment of the invention, the inorganic salts removed comprise at least potassium. As discussed hereinafter, removal of at least potassium can improve gasification as the presence of potassium in a gasifier can result in the production of a low melting point slag. Thus, according to certain embodiments, the biomass is processed to remove at least potassium therefrom. The amount of potassium in the processed biomass feedstock may be less than 2 wt %, less than 1 wt %, less than 0.75 wt %, less than 0.5 wt % or less than 0.25 wt % (w/w). Alternatively, less than 12 wt % of the total amount of ash in the processed biomass feedstock contains potassium, less than 10 wt %, less than 8 wt %, less than 6 wt % less than 5 wt % or less than 4 wt % (w/w).

As mentioned, extractives include organic acids. Examples of organic acids include acetic acid, galacturonic acid, formic acid, glucuronic acid and a combination thereof. Organic salts may include acetate, galacturonate, formate, glucuronate and a combination thereof. Byproducts include degradation products such as furfural, hydroxymethylfurfural (HMF) and furans, or fermentation byproducts such as lactic acid and glycerol.

In one embodiment of the invention, between 1 and 95 wt %, between 5 and 95 wt % or between 10 and 90 wt % (w/w) of the insoluble component of the biomass remains, i.e., is retained in the solids after the one or more processing steps. At least a portion of the lignin is typically retained when removing extractives, although a certain amount may become soluble. Between 0 and 90 wt % (w/w) of the lignin may become dissolved during the one or more processing steps. For example, dissolution of lignin may occur during an alkaline conditioning carried out prior to a pretreatment (see WO 2012/019305) or during a pretreatment process, as discussed below. A non-limiting example of a pretreatment that dissolves a portion of the lignin is sulfur dioxide pretreatment.

The weight ratio of water-to-feedstock (wt:wt) fed to the one or more processing steps that release extractives may be 0.5:1 to 25:1, 0.5:1 to 20:1, 0.5:1 to 15:1, 0.5:1 to 10:1, 0.5:1 to 5:1 as determined relative to the original biomass.

The one or more extractive releasing process steps may be catalyzed or uncatalyzed, and conducted with or without heat treatment. Such steps may include one or more pretreatment, meaning a step in which biomass is reacted under conditions that disrupt the fiber structure and that increase the susceptibility or accessibility of cellulose within the cellulosic fibers for a subsequent treatment. In further embodiments, the processing steps include preliminary treatments carried out prior to pretreatment. Non-limiting examples of pretreatment and optional preliminary treatments are set out further below.

A preliminary treatment step can be a pre-conditioning step, examples of which include (i) leaching, (ii) chemical treatment, including but not limited to alkali treatment, swelling or soaking, (iii) heat treatment, or a combination thereof.

Leaching is a process in which biomass or biomass derived material, either with or without size reduction, is contacted with a liquid to remove one or more extractives, such as salts. Contacting with the liquid, such as water, may be carried out by washing, spraying and the like. In this embodiment, the inorganic salts and other soluble components present in the biomass or biomass derived material are removed in a solids-liquid separation and a process stream comprising the salts may be sent to waste water treatment or recycled in the process.

Chemical treatment prior to pretreatment may involve the use of an alkali treatment to remove acetyl groups, swelling with alkali or soaking with acid. The chemical treatment may include chemical processes to solubilize or extract lignin, an example of which includes chemical pulping. Heat treatment may include the use of heat to treat the biomass at a temperature of above 80° C. This can involve a step of steaming or a soaking step with the application of heat. The biomass or biomass derived material may be heated with steam using direct steam treatment with mixing devices designed for introducing steam, and optionally additional chemical is added through spray nozzles.

After the optional preliminary treatment step or steps, the biomass or biomass derived material may be subjected to pretreatment. Pretreatment can be with heat, mechanical processing, addition of one or more chemicals, biocatalysts, or combinations thereof to release salts and/or solubilize components of the biomass, such as sugars. Pretreatment can be carried out with washing or leaching to remove soluble components as they are solubilized. After pretreatment, between 30 and 100 wt % of the xylan may be hydrolyzed, although there may be limited xylan hydrolysis during some pretreatments. After pretreatment, between 10 and 100 wt % of the lignin may remain insoluble.

Non-limiting examples of pretreatment include acid pretreatment, alkali pretreatment and hydrothermal pretreatment, each of which are discussed in turn below.

An acid pretreatment may be carried out at a maximum temperature of about 120° C. to about 280° C. The pH is generally below about 3. The time that the biomass is held at this temperature may be about 6 seconds to about 4 hours. The acid pretreatment produces a composition comprising an acid pretreated feedstock. Sugars produced by the hydrolysis of hemicellulose during acid pretreatment are generally present in the composition and include xylose, glucose, arabinose, mannose, galactose or a combination thereof. Organic acids may be present in the composition as well and may include acetic acid, galacturonic acid, formic acid, lactic acid, glucuronic acid or a combination thereof. Biomass or biomass derived material may contain hemicellulose with acetyl groups attached to xylan. Pretreatment processes typically liberate acetic acid from the acetyl groups.

An alkaline pretreatment can be with sodium hydroxide, potassium hydroxide, ammonia or other suitable alkali. The pH is generally above 9.

Examples of suitable alkaline pretreatment processes include ammonia fiber expansion (AFEX) or dilute ammonia pretreatment. According to the AFEX process, the biomass or biomass derived material is contacted with ammonia or ammonium hydroxide, which is typically concentrated, in a pressure vessel. The contact is maintained for a sufficient time to enable the ammonia or ammonium hydroxide to swell the cellulose fibers. The pressure is then rapidly reduced which allows the ammonia to flash or boil and explode the cellulose fiber structure. The flashed ammonia may then be recovered according to known processes. The AFEX process may be run at about 20° C. to about 150° C. or at about 20° C. to about 100° C. and all temperatures therebetween. The duration of this pretreatment may be about 1 minute to about 20 minutes, or any time therebetween.

Dilute ammonia pretreatment utilizes more dilute solutions of ammonia or ammonium hydroxide than AFEX. Such a pretreatment process may or may not produce any monosaccharides. Dilute ammonia pretreatment may be conducted at a temperature of about 100 to about 150° C. or any temperature therebetween. The duration for such a pretreatment may be about 1 minute to about 20 minutes, or any time therebetween.

A hydrothermal pretreatment can be carried out without the addition of pretreatment chemical, with the application of heat. An example of a suitable temperature for hydrothermal pretreatment is between about 80° C. and about 400° C., or between about 100° C. and about 350° C. Without being limiting, equipment that can be used to carry out hydrothermal pretreatment is an extruder. An example of hydrothermal pretreatment includes the application of heat to hydrolyze acetyl groups in the biomass or biomass derived material. A further example is hydrothermal carbonization of biomass or biomass derived material in a pressurized liquid at elevated temperatures, such as between 150° C. and 375° C., typically without oxygen or low levels thereof. Hydrothermal carbonization produces a material known as "hydrochar", which is a carbon-containing product that is typically solid having improved gasification properties. Optionally, the hydrochar can be densified as set forth herein.

Optionally, the foregoing processing steps are conducted as part of a cellulosic conversion process to produce a fuel or chemical, such as an alcohol and/or methane. Such a conversion process may include pretreating a biomass or biomass derived material comprising cellulose to disrupt fiber structure and improve accessibility of cellulose to a subsequent enzymatic or chemical treatment, enzymatic or chemical hydrolysis to hydrolyze cellulose to glucose, fermentation of sugars to a product and optionally concentration of the product by distillation. Enzymes may include cellulases, hemicellulases, amylases, glucanases, proteases, lipases, pectinases, laccases, phytases or combinations thereof. In one embodiment, the cellulose is hydrolyzed with cellulase enzymes.

In order to remove the released extractives, the present invention may comprise conducting a solids-liquid separation on a process stream comprising extractives and solids. The solids-liquid separation is any process in which liquid is removed from a process stream comprising the extractives and solids, thereby removing the extractives from insoluble components. The solids that are obtained comprise insoluble components derived from the biomass, which may include lignin. A stream comprising the solids may be subsequently provided to the gasification, as discussed further below.

An example of a stage in a cellulosic conversion process in which solids are removed is a solids-liquid separation carried out after enzymatic hydrolysis of a pretreated feedstock with cellulase. The solids obtained from such a solids-liquid separation comprise lignin and other insoluble components that are present after hydrolysis of cellulose by cellulase enzymes. Alternatively, the solids-liquid separation is conducted downstream of enzymatic hydrolysis, for example, after fermentation If the cellulosic conversion process involves distillation, the solids-liquid separation may be conducted downstream of distillation. Thus, the process of the invention may involve a solids-liquid separation at several locations, including upstream, downstream or both upstream and downstream of the distillation.

The solids-liquid separation may include mechanical methods such as centrifugation, filtering, pressing, including pressing that employs a screw or nip press, draining or sedimentation; chemical methods, such as the addition of flocculating agents; or thermal methods to remove water, such as drying, flashing or distillation. The filtering may include microfiltration, plate and frame filtration, cross-flow filtration, pressure filtration or vacuum filtration. Further, the solids-liquid separation can include a washing step within the separation.

The solids may comprise lignin and optionally other undissolved components such as cellulose, xylan or a combination thereof. In an embodiment of the invention, the solids comprise at least lignin and cellulose. The undissolved solids content of the solids after the separation can be between 5 and 70 wt %, or between 20 and 50 wt % (w/w). The undissolved solids content is measured as set forth previously.

In addition to removing potentially problematic components, it has been found that subjecting the biomass or biomass derived material to one or more processing steps to remove extractives can improve its heating value of the resultant processed biomass feedstock. In particular, results have shown that biomass that is not subjected to one or more processing steps to release extractives has a lower heating value (Btu/lb) than a biomass residue material that remains after enzymatic hydrolysis with cellulase or a lignin sample. (Example 1).

Thus, in further embodiments, the biomass or biomass derived material is subjected to one or more processing steps to produce a processed biomass feedstock having a net heating value (Btu/lb) that is higher than could otherwise be attained in the absence of carrying out the processing step(s). For example, the processed biomass feedstock may have a net calorific value, also referred to as a "lower heating value", of between about 5,000 and 15,000 Btu/lb, or between 6,000 and 11,000 Btu/lb. In an embodiment of the invention, the net calorific value is at least 6,000 Btu/lb, at least 6,500 Btu/lb, at least 7,000 Btu/lb or at least 7,200 Btu/lb.

(c) Densifying

Prior to gasification, the biomass or biomass derived material may be densified to produce a densified biomass feedstock. Densification can reduce transportation costs and typically increases the efficiency of the gasification process. It can also reduce dust production and simplify storage and handling infrastructure. The material that is densified may be the solids remaining after releasing extractives, mechanically treated biomass or biomass derived material, or biomass that has not been processed.

By "densified", it is meant that the bulk density of the densified biomass feedstock is between 5 and 100 lb/ft$^3$, between 8 and 75 lb/ft$^3$, or between 10 and 70 lb/ft$^3$. In certain embodiments, the biomass or biomass derived feedstock is densified or compressed to form densified material of defined shapes, such as pellets, briquettes, cubes, pucks, cylinders or other shapes. The densification may be carried out by mechanical densification, torrefaction or other methodologies as known to those of skill in the art.

The densified biomass feedstock will fall within a particular size distribution, measured by dry sieving the solids through screens of a defined size and shape. The size distribution is measured by passing the solids through round openings of a defined diameter. According to one embodiment of the invention, greater than 90% by weight of the densified or compressed solids are greater than ¼ inches in diameter, or greater than ⅜ inch. In one embodiment, 90% of the densified solids by weight are ¼ inch to 6 inches, ⅜ inch to 6 inches, ¼ inch to 5 inches, ⅜ inch to 5 inches, ¼ inch to 4 inches or between ⅜ to 3 inches in diameter.

Advantageously, the densification can improve the energy value of the processed biomass feedstock fed to the gasification reactor. By densifying biomass or biomass derived material, the energy per volume (Btu/ft$^3$) may be significantly improved, and in certain embodiments, the energy per volume can be higher than coal. (See Example 1). This can allow for improvements in volumetric feed rate to a gasifier, which in turn can allow a reactor to process feedstock at a higher rate. In addition, more energy per volume is gasified in the gasification reactor. Thus, co-gasifying coal and processed biomass feedstock could potentially improve the volumetric efficiency of the process over gasifying lignite coal alone. The energy value of densified biomass or biomass derived material may be further improved by removing extractives in one or more processing steps prior to densification, as discussed in Example 1. Thus, a process comprising combining the steps of removing extractives and densification can be used to provide material for densification with improvements in Btu/ft$^3$.

In further embodiments, a processed biomass feedstock is provided for gasification that possesses a suitable density without the need for conducting densification. For example, wood chips can be fed to the gasification without any processing steps subsequent to chipping.

Optionally, prior to densification, the biomass or biomass derived material has liquid removed therefrom. Between about 30 wt % and about 95 wt % (w/w) of the liquid may be removed from the biomass or biomass derived material prior to densification. The step of removing liquid from the biomass or biomass derived material may comprise a step of drying. The liquid content of the biomass or biomass derived material can also be increased prior to densification to achieve a desired moisture level. The biomass or biomass derived material can be subjected to steaming prior to or during densification. The application of steam, or the generation of heat from mechanical action can cause natural binding in the solids due to the release of components within the material.

Densification includes any of a variety of suitable methods to increase bulk density or heating value of the biomass or biomass derived material. Such methods include, without limitation, mechanical densification, torrefaction, pretreatment, or any combination of these methods. Optionally, a binder is added during densification. A binder can aid in allowing the densified solids to retain their shape after densification and may increase durability of the material upon physical handling.

Mechanical densification may involve the application of pressure to mechanically densify the biomass or biomass derived material. Non-limiting examples of processes for densifying the biomass or biomass derived material mechanically include extrusion and/or pressing.

During extrusion, the biomass or biomass derived material may be forced against a solid plate with openings formed in it. The material passes through the openings and conforms to the shape of the openings. A blade may be used to cut the material as it exits the dye. The temperature and/or pressure may be adjusted so that the solids fuse to form a solid mass. The densified biomass feedstock may then be cooled to a desired temperature. Examples of devices that make use of this principle are flat die pellet mills and ring die pellet mills.

In further embodiments, the biomass or biomass derived material may be fed to a roll press comprising rotating rolls. As the biomass or biomass derived material passes between the rolls they become compacted. The opposing rolls may each have depressions formed on the surface that contacts the opposing roll. As the solids pass between the roll presses, they conform to the shape of the depressions formed upon contact of the depressions. The densified biomass feedstock that exits the press will have a shape that corresponds to that of the two opposing depressions. Such a process is referred to as roll press briquetting.

Another method for densifying the biomass or biomass derived material is a compression press that uses a cylinder to generate a compressive force. The reciprocating action of the cylinder compacts the biomass or biomass derived material into a die under pressure. The piston press may operate using hydraulics or an electric motor.

In a further embodiment, the biomass or biomass derived material is fed to a screw press that removes liquid by an axially mounted screw that rotates within a shell containing passages through which liquid can pass, but that retains most of the solids. The rotatable screw may have increasing cross-sectional area from the inlet to the outlet thereof.

Torrefaction can be used to increase the density of biomass or biomass derived material. Torrefaction involves heating biomass or biomass derived material at elevated temperature, typically in an environment with low levels of oxygen, and may release water and volatile organic compounds, thereby improving the gross calorific value of biomass or biomass derived material and/or its friability. An example of a suitable temperature for torrefaction is between 280° C. and 320° C. Torrefaction is optionally carried out prior to a mechanical densification.

Other treatments, such as pretreatment can be conducted to increase the density of the biomass or biomass derived material. Disrupting biomass or biomass derived material by a pretreatment may improve the physical characteristics of densified material. An example of a suitable pretreatment is steam explosion. U.S. Pat. No. 4,461,648 (Foody) describes equipment and conditions used in steam explosion pretreatment, in which the feedstock, steam, and optionally pretreatment chemical are added to a reaction vessel, known as a steam gun. In the steam gun, steam is added and the steam pressure is increased rapidly to the desired pressure, held at this pressure for a period of time, followed by sudden explosive decompression. Steam explosion, or other pretreatment process can optionally be combined with mechanical densification.

Gasification

The processed biomass feedstock is subsequently subjected to gasification to produce a gaseous product comprising carbon monoxide and hydrogen, also referred to herein as "syngas", and cresylic acid. The gaseous product may comprise other gaseous components in addition to carbon monoxide and hydrogen, such as carbon dioxide and methane. Most of the carbon dioxide is generally removed, to produce a stream comprising predominantly carbon monoxide and hydrogen (syngas). As set forth below, the syngas can be reacted to produce a fuel or fuel intermediate.

The gasification includes heating at elevated temperature to produce the syngas. Gasification is typically carried out in the presence of oxygen. According to an embodiment of the invention, gasification is not part of a combustion process to generate heat energy or electricity.

As set out previously, the use of processed biomass feedstock from which at least a portion of the extractives has been removed has the advantage that less undesirable components are produced during the gasification.

In particular, the chemical composition of the ash can result in operational problems. Without being limited by theory, potassium is a component of ash that can combine with silica and lower the melting temperature of the ash, known in the art as the "ash fusion temperature" which is measured in accordance with ASTM D1857M. The result is the formation of slag that forms a mobile phase under the gasification conditions. This is particularly problematic in non-slagging reactors in which ash is removed in a dry condition as such reactors are not designed to handle slag. The flowing slag can lead to fouling of gasification units in which dry ash is removed, requiring shut-downs and expensive cleaning.

As discussed, it can be desirable to remove at least a portion of potassium from the biomass or biomass derived material to prevent such slag formation. In certain embodiments, the processed biomass feedstock has an amount of potassium removed therefrom to elevate the ash fusion temperature of ash formed during gasification so it is higher than the operating temperature of the gasification, preferably at least 5° C. higher.

Another advantage of using the processed biomass feedstock from which extractives have been removed is that chloride is reduced or eliminated. Chloride is corrosive to certain metals commonly used in gasification equipment and thus, by reducing the concentration of this component, the process equipment is less prone to corrosion or need not be constructed with corrosion resistant material. Chloride may be present in the processed biomass feedstock at a concentration of less than 2 wt % or 1 wt % relative to the ash content. Chloride is measured by potentiometric titration.

In certain embodiments of the invention, the processed biomass feedstock is gasified in a gasification plant that is capable of using coal as a feed. The coal includes any grade of coal suitable for gasification and may include lignite, sub-bituminous coal, bituminous coal, steam coal, or anthracite coal. In one embodiment of the invention, the coal is lignite. Some gasifiers can be used with a wide range of coal types, ranging from anthracite to lignite.

As used herein, the term "gasification plant" refers to an operation in which a process is carried out comprising producing syngas by gasification in one or more gasification reactors.

The gasification may be performed in reactors with different types of solid-gas contact, including reactors with beds that are moving, fluidized, entrained or contain melting salts. In an embodiment of the invention, the gasifier is non-slagging, meaning that it operates at temperatures at which no or limited slagging of ash occurs.

A moving bed reactor may be preferred due to its high thermal efficiency and conversion and suitability for cresylic acid production. An example of such a reactor is a Lurgi-type reactor, which includes reactors designed by Lurgi or reactors adapted from a Lurgi design. The processed biomass feedstock may be fed through the top of the reactor, while gasifying agents, such as air or oxygen are fed through the bottom of the reactor. The solids and gasifying agents come into contact with one another counter-currently. Solid ash is removed through a grate or taphole in the bottom of the reactor. In an embodiment of the invention, the reactor is pressurized. Moving bed reactors operate at elevated pressure. Such reactors may utilize pressure locks to feed coal into the top of the reactor. Processed biomass feedstock that is densified is well suited to replace solid coal in such pressurized reactors.

Moving bed reactors, including Lurgi-type reactors, may also be particularly well suited for cresylic acid production due to their counter-current nature and temperature profile. Processing a tar stream at above 1000° C. may decrease cresylic acid yield. Since cresylic acid is derived from tar, gasifying in lower temperature gasifiers may thus offer benefits in terms of obtaining a higher yield of cresylic acid. Further, processing at temperatures below about 1000° C. can reduce slag formation. Thus, in one particularly advantageous embodiment of the invention, the gasifier is a non-slagging gasifier, which refers to a gasifier operated under conditions so that the ash does not form a mobile phase. In a further embodiment of the invention, the gasifier is a moving bed reactor or a Lurgi-type reactor.

In an embodiment of the invention, the temperature range of the gasification may be between 500 and 1500° C., between 500 and 1400° C., between 500 and 1350° C., between 500 and 1200° C. or between 500 and 1100° C., which is measured at the hottest point in the gasifier. As would be appreciated by those of skill in the art, the hottest point in a gasifier varies according to the particular type of reactor employed. In both moving and fluidized bed reactors, the temperature is highest in a mid-region of the gasifier, while the inlet in which coal is introduced and the outlet where ash is discharged operate at lower temperatures. The hottest point in a moving-bed gasifier, such as a Lurgi-type reactor, is in a mid-region of the gasifier, above a grate or taphole, which discharges ash to a bottom region of the gasifier. The hottest point of a fluidized bed reactor is within a mid-region of the gasifier bed. The temperature of an entrained-flow gasifier can be measured at an outlet where gas or slag is discharged since the temperature does not vary between the bed and these outlets.

In further embodiments, the gasification process produces carbon dioxide as a byproduct. The carbon dioxide may be introduced to a carbon dioxide pipeline. The process may thus further comprise withdrawing or causing withdrawal of an amount of carbon dioxide from the pipeline for introduction underground. For example the carbon dioxide may be introduced underground for extracting oil or gas in an enhanced oil or gas recovery. Introducing carbon dioxide underground reduces the life cycle GHG emissions of a product for use as a liquid transportation or heating fuel produced or derived from the gasification.

The processed biomass feedstock may be co-gasified with coal. By co-gasification, it is meant that the processed biomass feedstock and coal are either co-fed to a gasification reactor or fed alternately with the coal at different intervals within a particular period of time. The coal and processed biomass feedstock may be combined and fed to the gasifier or fed as separate streams.

Co-gasifying processed biomass feedstock with coal may provide benefits over operating a gasification plant in which such feedstock is used exclusively as the starting material. Replacing a portion of coal fed to a coal gasification plant with processed biomass feedstock can benefit from the efficacy of the biomass gasification and the dependability of the coal gasification technology. Moreover, replacing coal with processed biomass feedstock at an existing coal gasification plant provides the opportunity for biomass feedstock to be utilized on a commercial scale, which offers capital and operating cost benefits. Operating at the large scale of an industrial coal gasification plant may not be possible for a dedicated biomass gasification plant because the infrastructure and cost for coal supply can support much larger facilities than with biomass alone. Thus, co-gasifying can overcome some of the shortcomings of using biomass in gasification, thereby promoting commercialization of producing fuels and other products from these feedstocks.

Further, co-gasifying processed biomass feedstock with coal can reduce the GHG emissions of fuel or fuel intermediate products obtained or derived from gasification and can result in advantaged fuel credit generation, as discussed hereinafter. Co-gasifying coal with the processed biomass feedstock means that less coal is used in or supplied to the gasification plant than would otherwise be the case as a result of the use or supply to such plant of the processed biomass feedstock. The use of processed biomass feedstock in the gasification may thus avoid extraction of an amount of coal from underground reservoirs or deposits. In one embodiment, co-gasifying results in a reduction in the use of coal at the gasification plant that is otherwise available for use therein resulting from taking coal out of use at the gasification plant.

In examples of the invention, co-gasifying may also potentially improve the yield of cresylic acid recovered during gasification. For example, the yield of cresylic acid could potentially, in certain embodiments, be increased above baseline levels, for example by at least 1%, 5%, 10% or 20% by using a mix of processed biomass feedstock in a coal feed stream. The baseline is the yield of cresylic acid by using lignite coal alone as the feedstock to gasification. In certain embodiments of the invention, the yield of cresylic acid is increased from 1% to 1200%, 5% to 1000% or 20% to 1000% relative to lignite coal.

In further embodiments of the invention, co-gasifying processed biomass feedstock with coal may involve co-feeding or co-processing coal and processed biomass feedstock, such that at least 1% or at least 2% of the stream fed to gasification is processed biomass feedstock, or at least 4% of the stream is processed biomass feedstock by energy content (Btu). In further embodiments, co-processing processed biomass feedstock with coal involves co-feeding coal and processed biomass feedstock such that between 1% and 80% by weight of the stream is processed biomass feedstock, or between 2% and 70% or between 4% and 30% by energy content is processed biomass feedstock.

An advantage of co-gasifying is that the feed to the gasification can be varied depending on the properties of the coal and processed biomass feedstock. The gasification properties of coal and the processed biomass feedstock can vary quite significantly, depending upon the shipment. The ability to blend the processed biomass feedstock with coal provides additional flexibility in terms of balancing the properties of each feedstock to achieve a feedstock blend to gasification having a desired composition. Thus, the ability to co-process processed biomass feedstock and coal allows a gasification plant to manage changes in the feedstock to counterbalance undesirable properties in the coal or processed biomass feedstock. This may also allow a plant to optimize the amount of processed biomass feedstock that is fed to the gasification reactor. By way of example, the chemical make-up of the coal can vary, in particular the ash content. If the sodium content of a batch of coal is high, more processed biomass feedstock that has lower levels of sodium can be added to the feed such as wheat straw or corn stover. According to further embodiments, blending more processed biomass feedstock with coal could potentially be utilized as a methodology to increase tar production. This in turn could result in improvements in cresylic acid production, as it is a phenolic mixture derived from tar.

Product for Use as Transportation or Heating Fuel

The process of the invention involves providing one or more products, for use as, or to produce a transportation or heating fuel which has reduced life cycle GHG emissions relative to a gasoline baseline. As used herein "products" are hydrogen, syngas, or a fuel or fuel intermediate produced directly or indirectly from syngas, examples of which include gaseous fuels, alcohols and liquid hydrocarbons. Providing a product includes supplying, or directly or indirectly causing, one or more parties to supply the product to an entity for use as a transportation or heating fuel or as an intermediate to produce such fuels.

The term "cause" or "causing", as used throughout the specification means to arrange or bring about, either directly or indirectly, or to play a required role in a series of activities through commercial arrangements such as a written agreement, verbal agreement or contract.

If hydrogen is recovered, it may be separated from the syngas. Alternatively, the carbon monoxide in the syngas may undergo a water gas shift reaction where more hydrogen is produced by additional reaction with water according to the following chemical reaction:

$$CO + H_2O \rightarrow CO_2 + H_2.$$

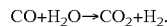

In certain embodiments, the hydrogen produced by this reaction is referred to as renewable or partially renewable hydrogen.

It is preferred that the hydrogen be purified to remove one or more non-hydrogen components. The hydrogen may be recovered by methods known to those skilled in the art to produce a recovered hydrogen product, such as a liquid absorption system for carbon dioxide removal or a pressure swing absorption operation.

It should be understood that if renewable or partially renewable hydrogen is introduced to an apparatus such as a pipeline, a substantially equal amount of hydrogen withdrawn will still be considered renewable or partially renewable by regulators. According to such embodiment, an amount of hydrogen withdrawn from the apparatus will be considered to have the GHG emission attributes of an amount introduced that is produced from the syngas, despite that the hydrogen may not contain actual molecules from the original cellulosic feedstock.

Renewable hydrogen may be used directly as a product for use as a transportation or heating fuel or can be used in any stage of a process to produce another product for such use. In one embodiment, hydrogen is used as a transportation fuel in a modified combustion engine. The renewable hydrogen may alternatively be used in a process to produce a product for use as a liquid transportation or heating fuel. According to such embodiment, the renewable hydrogen may be withdrawn from a pipeline or other apparatus for transporting same and combined with a crude oil derived liquid hydrocarbon so that it becomes incorporated into the hydrocarbon and becomes part of a liquid transportation or heating fuel. An example of such a process is set forth in co-owned U.S. Pat. No. 8,658,026 (Brian Foody and Patrick J. Foody), which is incorporated herein by reference in its entirety.

The carbon monoxide and hydrogen (syngas) may be reacted produce a fuel or fuel intermediate. Fuels or fuel intermediates made from syngas may include gaseous fuels, alcohols or liquid hydrocarbons. Examples include methane, hydrogen, dimethyl ether, methanol, acetic acid, acetate, ethanol, butanol, and liquid hydrocarbons.

In an embodiment of the invention, methane is produced from syngas, which may also be considered biomethane or renewable. The production of methane from syngas includes a methanation reaction, which is typically conducted over a metal catalyst at elevated temperature and pressure. The chemical reaction for producing methane from syngas is as follows:

$$CO + 3H_2 \rightarrow CH_4 + H_2O.$$

The gasification to produce syngas may be carried out together with methanation in the same reactor. Such processes are known in the art as hydromethanation.

Methanation results the production of methane, along with a mixture of gases. One or more impurities from the methane can be removed. An example of such a technique is a Rectisol operation. Carbon dioxide removed from the mixture of gases can be fed to a carbon dioxide pipeline and used in an enhanced oil or gas recovery operation.

The methane resulting from the above methanation reaction can be introduced to an apparatus for transporting methane. An amount of methane withdrawn from the apparatus has the GHG emission attributes of the amount of methane produced from the syngas introduced to the apparatus, as discussed previously in connection with hydrogen. According to certain embodiments of the invention, this amount of methane withdrawn is considered renewable or partially renewable.

The methane may be used directly as a product for use as a transportation or heating fuel, or can be used as to produce another fuel. The methane may be introduced to a pipeline as discussed above.

The withdrawn methane can be used to make renewable hydrogen and the renewable hydrogen can be used to hydrogenate a crude oil derived liquid hydrocarbon as set out in U.S. Pat. No. 8,658,026 (supra).

The syngas can also be used to make a fuel or fuel intermediate by a Fischer Tropsch process. A Fischer Tropsch process uses a catalyst to convert carbon monoxide to hydrocarbons, such as alkanes, although other reaction products may result as well. The alkanes can be used as transportation or heating fuels. Moreover, some microorganisms can produce fuels or fuel intermediates by utilization of syngas. Microorganisms, such as acetogens, can convert syngas into ethanol, butanol, and methane that can be used as transportation or heating fuel or used in processes to produce such a fuel.

Syngas can also be converted to an alcohol, such as methanol. The methanol can be used as a transportation or heating fuel or can be converted into further products that can be used in transport or heating. For example, methanol can be converted to methyl esters by reaction with natural fats and oils to produce methyl esters and glycerin. The methyl esters can be used to make biodiesel. The methanol can also be converted to gasoline by converting methanol to dimethyl ether by a dehydration reaction. Subsequently, an equilibrium mixture of methanol, dimethylether and water is converted to short-chain olefins. In a further reaction step, the short-chain olefins are reacted to form higher olefins, including n/iso-paraffins, aromatics and napththenes.

In one advantageous embodiment of the invention, syngas is used to produce ethanol. According to such embodiment, syngas can be reacted to produce methanol, which can be subsequently reacted with carbon monoxide to produce acetic acid or acetate. The acetic acid or acetate in turn can be reacted with hydrogen to produce ethanol.

Recovery of Cresylic Acid

As mentioned, cresylic acid is produced during the gasification and is recovered. Recovering cresylic acid comprises obtaining a stream comprising at least o-cresol, m-cresol or p-cresol for further use. Typically, the cresylic acid is recovered in a purified form.

During the gasification, one or more liquid streams may be formed from gas cooling and/or scrubbing that comprise cresylic acid. Without being limiting, often a high excess of steam is required during gasification in relation to the requirements for stoichiometry in order to obtain high conversion rates. The gas thus obtained may contain significant amounts of steam. In order to remove the steam, the gas may be cooled so that the water condenses. The condensed liquid can then be separated out as a condensate stream. Cooling can also be achieved by quenching the gas with a water stream or potentially the liquid stream may arise from scrubbing. A liquid stream resulting from gasification is referred to herein as a "liquid gasification stream".

These liquid streams comprise components originating from tar such as phenolic products. Tar may arise from volatile matter in the feedstock. The phenolic products may include aromatic compounds with one or multiple hydroxyl groups, termed mono-hydric phenols and poly-hydric phenols, respectively. The phenolic products originate from tar produced during the gasification and comprise cresylic acid.

The cresylic acid may be a mixture of monohydric phenols including predominantly meta-cresol, para-cresol and ortho-cresol. In addition, the cresylic acid may comprise other phenolics such as xylenols and/or ethylphenols.

Impurities that are present may include water, guaiacol, dihydric phenols, pitch, neutral oil and tar bases, among other components.

Cresylic acid or a portion thereof is recovered from the liquid gasification stream, typically by a combination of extraction and distillation. During extraction, the liquid gasification stream may be subjected to a chemical extraction to extract the phenolic products from water. A non-limiting example of such an extraction process is the Phenosolvan process which utilizes diisopropyl ether or a similar solvent as the extraction solvent. The solvent can be subsequently distilled and recycled. The extraction typically results in a mixture of crude phenolics, which comprises cresylic acid and may also contain water, guaiacol, dihydric phenols, pitch, neutral oil and tar bases.

Distillation may be carried out to further purify the mixture of crude phenolics by removing dihydric phenols and pitch. After distillation, a stream will be obtained comprising cresylic acid, tar bases and neutral oil. The tar bases and neutral oil can then be removed by one or more further distillation steps.

It will be appreciated, however, that the invention is not restricted in scope to the foregoing recovery techniques and encompasses alternative or additional processes for recovering cresylic acid.

Cresylic acid that is recovered may include cresols selected from ortho-cresol, meta-cresol, para-cresol, and combinations thereof. Typically, other phenolics will be present as well, including ethylphenol and/or xylenol. Impurities may be present as well including water, guaiacol, dihydric phenols, neutral oils, tar bases, sulfur compounds and other substances (such as pitch, methyl substituted guaiacols, C10 phenolics, non-catechol dihydroxy phenols and unidentified nitrogen compounds).

Cresylic acid has various industrial uses. Mixed cresols can be used as wire enamel solvents, disinfectants and preservatives, o-cresol finds use as a solvent, disinfectant and chemical intermediate, m-cresol can be used to produce herbicides, insecticides, antioxidants and explosives, while p-cresol is used in the formulation of antioxidants and in the fragrance and dye industries (EPA cresol article).

Determining Life Cycle GHG Emissions

The use of the processed biomass feedstock in gasification reduces the GHG emissions associated with products produced by the process, which may enable advantaged fuel credit generation. According to certain embodiments of the invention, the product produced in accordance with the invention for use as a transportation or heating fuel has life cycle GHG emissions associated therewith that are at least 20%, 30% or 40% lower than a gasoline baseline. However, in certain embodiments, these savings can be at least as much as 50% lower than a gasoline baseline, or even at least as much as 60%, 70%, 80%, 90% or 100% lower than a gasoline baseline. The GHG emission reductions can be further reduced by using carbon dioxide produced as a byproduct in the gasification in an application involving the introduction of carbon dioxide underground, such as enhanced oil or gas recovery.

To determine life cycle GHG emissions associated with a product for use as transportation or heating fuel, analyses are conducted to calculate the GHG emissions related to the production and use of the fuel throughout its life cycle. Life cycle GHG emissions include the aggregate quantity of GHG emissions related to the full life cycle of the transportation or heating fuel, including all stages of fuel and feedstock production and distribution, from feedstock generation or extraction through the distribution and delivery and use of the finished fuel to the ultimate consumer. GHG emissions account for total net GHG emissions, both direct and indirect, associated with feedstock production and distribution, the fuel production and distribution and use.

Because many of the laws adopted differentiate the requirements for fuels based upon their net GHG emissions impacts, it is known to those skilled in the art that regulators have developed and/or adopted methods to analyze and characterize the expected net GHG emissions of fuel pathways. Thus, according to certain embodiments of the invention, life cycle GHG emissions are determined in accordance with prevailing rules and regulations.

Examples of Methodologies for Calculating Life Cycle GHG Emissions

Life cycle GHG emissions evaluations generally consider GHG emissions associated with each of:
a) feedstock production and recovery, including the source of carbon in the feedstock, direct impacts such as chemical inputs, energy inputs, and emissions from the collection and recovery operations, and indirect impacts such as the impact of land use changes from incremental feedstock production;
b) feedstock transport, including feedstock production and recovery and GHG emissions from feedstock transport including energy inputs and emissions from transport;
c) fuel production, including chemical and energy inputs, emissions and byproducts from fuel production (including direct and indirect impacts); and
d) transport and storage of the fuel prior to use as a transportation or heating fuel, including chemical and energy inputs and emissions from transport and storage.

Examples of models to measure life cycle GHG emissions associated with the one or more products of the invention, include, but are not limited to:

i) GREET Model—GHGs, Regulated Emissions, and Energy Use in Transportation, the spread-sheet analysis tool developed by Argonne National Laboratories;
ii) FASOM Model—a partial equilibrium economic model of the U.S. forest and agricultural sectors developed by Texas A&M University;
iii) FAPRI International Model—a worldwide agricultural sector economic model that was run by the Center for Agricultural and Rural Development ("CARD") at Iowa State University;
iv) GTAP Model—the Global Trade Analysis Project model, a multi-region, multi-sector computable general equilibrium model that estimates changes in world agricultural production as well as multiple additional models; and
v) ISO (International Organization for Standardization) standards for GHG emissions accounting and verification—provides guidance for quantification, monitoring and reporting of activities intended to cause greenhouse gas (GHG) emission reductions or removal enhancements.

The life cycle GHG emissions or carbon intensity of the products of the invention are measured in carbon dioxide equivalents ($CO_2$eq). As would be understood by those of skill in the art, carbon dioxide equivalents are used to compare the emissions from various GHGs based upon their global warming potential (GWP), which is a conversion factor that varies depending on the gas. The carbon dioxide equivalent for a gas is derived by multiplying the amount of the gas by the associated GWP.

$$\text{grams of } CO_2\text{eq}=((\text{grams of a gas})*(\text{GWP of the gas}))$$

The GWP conversion value used to determine g $CO_2$eq will depend on applicable regulations for calculating life cycle GHG emissions reductions. The GWP under EISA is 1, 21 and 310, respectively, for carbon dioxide, methane and nitrous oxide as set forth in Renewable Fuel Standard Program (RFS2) Regulatory Impact Analysis, February 2010, United States Environmental Protection Agency, EPA-420-R-10-006, pg. 13, of which the entire contents are incorporated herein by reference. Under California's LCFS, the GWP is 1, 25 and 298, respectively, for carbon dioxide, methane and nitrous oxide, as measured by the GREET model. It should be appreciated, however, that GWP values can change depending on prevailing regulations.

The unit of measure for carbon intensity or life cycle GHG emissions that may be used to quantify GHG emissions of the product of the present invention is grams $CO_2$eq per MJ of energy in the fuel or grams $CO_2$eq per million British thermal units of energy in the fuel (MMBTU). The units used to measure life cycle GHG emissions will generally depend on applicable regulations. For example, under the EPA regulations, GHG emissions are measured in units of grams $CO_2$eq per million BTUs (MMBTU) of energy in the fuel. Under LCFS, GHG emissions are measured in units of grams $CO_2$eq per MJ of energy in the fuel and are referred to as carbon intensity or CI.

The life cycle GHG emissions of the product of the invention are compared to the life cycle GHG emissions for gasoline, referred to as a gasoline baseline. GHG life cycle emissions are compared by reference to the use of gasoline per unit of fuel energy.

The value of the gasoline baseline used in life cycle GHG emission calculations can depend on the regulatory body. The EPA measures the carbon intensity of gasoline (gasoline baseline) as 98,204 g $CO_2$eq/MMBTU or 93.10 g $CO_2$eq/

MJ. Under California's LCFS, the gasoline baseline is 95.86 g $CO_2$eq/MJ. Those of ordinary skill in the art can readily convert values herein from g $CO_2$eq/MJ to g $CO_2$eq/MMBTU or g $CO_2$eq/MMBTU to g $CO_2$eq/MJ by using an appropriate conversion factor. Further, it should be appreciated that the value for the gasoline baseline can change over time depending on prevailing regulations.

According to certain embodiments of the invention, the life cycle GHG emission reduction relative to a gasoline baseline is measured "using EPA methodology", which means measuring life cycle GHG emissions reductions as disclosed in EPA-420-R-10-006, or supplanted by prevailing methodologies used by the EPA, which are publicly available.

According to a further embodiment of the invention, the life cycle GHG emission reduction relative to a gasoline baseline is measured using "LCFS methodology", which means measuring life cycle GHG emissions reductions by California's LCFS methodology using the GREET model, as set forth in Detailed California-Modified GREET Pathway for Corn Ethanol, California Environmental Protection Agency, Air Resources Board, Jan. 20, 2009, Version 2.0, or supplanted by prevailing methodologies used by regulators, which are publicly available.

According to one embodiment of the invention, the life cycle carbon dioxide emissions, rather than the life cycle GHG emissions, are determined for the one or more products of the invention for use as a transportation or heating fuel and compared to a gasoline baseline. For example, in those embodiments in which a reduction in carbon dioxide emissions relative to a production process baseline is quantified, a life cycle carbon dioxide emission reduction can be quantified instead of a life cycle GHG emission reduction.

Meeting Renewable and Low Carbon Fuel Targets

The invention advantageously provides a methodology for meeting renewable fuel targets or mandates established by governments, including legislation and regulations for transportation or heating fuel sold or introduced into commerce in the United States. Examples of such legislation include the Energy Independence and Security Act ("EISA") and California AB 32—The Global Warming Solutions Act, which respectively established an RFS and a Low Carbon Fuel Standard (LCFS). For example, under EISA, the mandated annual targets of renewable content in fuel are implemented through an RFS that uses tradable credits (called Renewable Identification Numbers, referred to herein as "RINs") to track and manage the production, distribution and use of renewable fuels for transportation or other purposes. Targets under the LCFS can be met by trading of credits generated from the use of fuels with a lower GHG emission value than the gasoline baseline.

The term "credit", "renewable fuel credit" or "fuel credit" means any rights, credits, revenues, offsets, greenhouse gas rights or similar rights related to carbon credits, rights to any greenhouse gas emission reductions, carbon-related credits or equivalent arising from emission reduction trading or any quantifiable benefits (including recognition, award or allocation of credits, allowances, permits or other tangible rights), whether created from or through a governmental authority, a private contract or otherwise. According to one embodiment of the invention, the renewable fuel credit is a certificate, record, serial number or guarantee, in any form, including electronic, which evidences production of a quantity of fuel meeting certain life cycle GHG emission reductions relative to a baseline set by a government authority. Preferably, the baseline is a gasoline baseline. Non-limiting examples of credits include RINs and LCFS credits in the United States.

The fuel credit may be generated in connection with the one or more of the products from syngas, or a product derived therefrom that is used as a transportation or heating fuel. According to an embodiment of the invention, a fuel credit is generated or caused to be generated with respect to the use of methane as a transportation or heating fuel.

In one embodiment, the product of the invention could qualify for an advanced biofuel RIN under EISA having a D code of 3, 4, 5 or 7. In a further embodiment, the product of the invention is eligible for a RIN having a D code of 3 or 5. Under the LCFS, products for use as fuels with greater reductions in life cycle GHG emissions qualify for a greater number of credits having higher market value than fuels with lower reductions.

Energy policy, including EISA and LCFS, and the generation of renewable fuel credits under each of these legislative frameworks, is discussed in turn below.

(a) Meeting Renewable Fuel Targets Under EISA

U.S. policymakers have introduced a combination of policies to support the production and consumption of biofuels, one of which includes the RFS. The RFS originated with the Energy Policy Act of 2005 (known as RFS1) and was expanded and extended by the EISA of 2007. The RFS expanded and extended under EISA is sometimes referred to as RFS2 or RFS as used herein.

Under the EISA, the RFS sets annual mandates for renewable fuels sold or introduced into commerce in the United States through 2022 for different categories of biofuels (see Table 2 below). There is an annually increasing schedule for minimum aggregate use of total renewable biofuel (comprised of conventional biofuels and advanced biofuels), total advanced biofuel (comprised of cellulosic biofuels, biomass-based diesel, and other advanced biofuels), cellulosic biofuel and bio-based diesel. The RFS mandates are prorated down to "obligated parties", including individual gasoline and diesel producers and/or importers, based on their annual production and/or imports.

Each year, obligated parties are required to meet their prorated share of the RFS mandates by accumulating credits known as RINs, either through blending designated quantities of different categories of biofuels, or by purchasing from others the RINs of the required biofuel categories.

The RIN system was created by the EPA to facilitate compliance with the RFS. Credits called RINs are used as a currency for credit trading and compliance. RINs are generated by producers and importers of renewable biofuels and assigned to the volumes of renewable fuels transferred into the fuel pool. RINs are transferred with a fuel through the distribution system until they are separated from the fuel by parties who are entitled to make such separation (generally refiners, importers, or parties that blend renewable fuels into finished fuels). After separation, RINs may be used for RFS compliance, held for future compliance, or traded. There is a centralized trading system administered by the U.S. EPA to manage the recording and transfer of all RINs.

According to certain embodiments of the invention, a RIN may be characterized as numerical information. The RIN numbering system was in the format KYYYYCCCCFFFFF-BBBBBRRDSSSSSSSSEEEEEEEE where numbers are used to designate a code representing whether the RIN is separated from or attached to a specific volume (K), the calendar year of production or import (YYYY), Company ID (CCCC), Facility ID (FFFFF), Batch Number (BBBBB), a code for fuel equivalence value of the fuel (RR), a code for the renewable fuel category (D), the start of the RIN block (SSSSSSSS) and the end of the RIN block (EEEEEEEE) Under current regulations, a RIN contains much of the foregoing information and other information in the form of data elements that are introduced into a web-based system administered by the EPA known as the EPA Moderated Transaction System, or "EMTS". It should be appreciated, however, that the information required for RIN generation and/or the format of the information may change depending on prevailing regulations.

The D code of a RIN specifies the fuel type, feedstock and production process requirements and thus in certain embodiments of the invention the D code may be used to characterize the type of RIN, as set out hereinafter. The D code of a RIN is assigned a value between 3 and 7 under current regulations. The value assigned depends on the fuel type, feedstock and production process requirements as set out in Table 1 to 40 C.F.R. §80.1426. Examples of fuels assigned a D code of 3-7 under current regulations are provided below. These examples are for illustration purposes only and are not to be considered limiting to the invention.

TABLE 1

RIN D code examples

| D code | Fuel Type | Example |
| --- | --- | --- |
| 3 | Cellulosic biofuel | Ethanol from cellulosic biomass from agricultural residues |
| 4 | Biomass-based diesel | Biodiesel and renewable diesel from soy bean oil |
| 5 | Advanced biofuel | Ethanol from sugarcane |
| 6 | Renewable fuel (conventional biofuel) | Ethanol from corn starch |
| 7 | Cellulosic diesel | Diesel from cellulosic biomass from agricultural residues |

As set out previously, the RFS2 mandate volumes are set by four separate but nested category groups, namely renewable biofuel, advanced biofuel, cellulosic biofuel and biomass-based diesel. The requirements for each of the nested category groups are provided in Table 2.

The nested category groups are differentiated by the D code of a RIN. To qualify as a total advanced biofuel, the D code assigned to the fuel is 3, 4, 5 or 7, while to qualify as cellulosic biofuel the D code assigned to the fuel is 3 or 7 (Table 2).

According to current regulations, each of the four nested category groups requires a performance threshold in terms of GHG reduction for the fuel type. In order to qualify as a renewable biofuel, a fuel is required to meet a 20% life cycle GHG emission reduction (or be exempt from this requirement), while advanced biofuel and biomass-based diesel are required to meet a 50% life cycle GHG emission reduction and cellulosic biofuels are required meet a 60% life cycle GHG emission reduction, relative to a gasoline baseline. As well, each nested category group is subject to meeting certain feedstock criteria.

TABLE 2

Nested category groups under RFS2

| Nested category group | Fuel type | Life cycle GHG threshold reduction relative to gasoline baseline |
| --- | --- | --- |
| Renewable biofuel | Conventional biofuels (D code 6) and advanced biofuels (D code 3, 4, 5 or 7) | 20% |
| Advanced biofuel | Cellulosic biofuels (D code 3 or 7), biomass-based diesel (D code 4 or 7), and other advanced biofuels (D code 5) | 50% |
| Cellulosic biofuels | Biofuel derived from cellulosic material (D code 3) and bio-diesel derived cellulosic material (D code 7). | 60% |
| Biomass-based diesel | Conventional biodiesel (D code 4) or cellulosic diesel (D code 7) | 50% |

Thus, according to certain embodiments of the invention, a RIN credit containing information or a value corresponding to a reduction in life cycle GHG emissions relative to a baseline is generated with the production of a volume of one or more products produced by the process. The information may correspond to a reduction in life cycle GHG emissions of at least 40, 45, 50, 55, 60, 65, 70, 75, 80 or 85% relative to a gasoline baseline. The invention may contribute wholly or in part to achieving reductions in the life cycle GHG emissions of a product for use as a fuel relative to a gasoline baseline.

The RIN associated with one or more products obtained or derived from the process may be assigned a D code of 3, 4, 5 or 7, also referred to herein as a D3, D4, D5 and D7 RIN, respectively. According to certain embodiments, the RIN associated with the one or more products may be assigned a D code of 3 or 5. Under current regulations, this corresponds to cellulosic biofuel and advanced biofuel fuel types, which meet GHG emissions reductions of 60% and 50%, respectively, relative to a gasoline baseline.

According to some embodiments of the invention, the fuel credit is characterized as containing numerical information associated with the one or more products produced by the process of the invention for use as a transportation or heating fuel. Thus, a party may generate a fuel credit comprising numerical information relating to one or more products of the process representing at least one parameter selected from (i) the type of transportation or heating fuel; (ii) the year in which the product was produced; (iii) a registration number associated with the producer or importer; and (iv) serial number associated with a batch. In a further embodiment, at least two parameters or at least three parameters are selected from the foregoing list. The numerical information may also include one or more of the following parameters selected from: (i') a number identifying that the numerical information is assigned to a volume of the product, or separated; (ii') a registration number associated with the facility at which the product was produced or imported; (iii') a number representing a value related to an equivalence value of the product; (iv') a number representing a first-volume numerical information associated with a batch of the product; and (v') a number representing a last-volume numerical information associated with a batch of the product.

The RIN or numerical information described herein or portion thereof is provided to a government regulatory agency, including the EPA, in connection with generating a RIN. In some embodiments of the invention, the numerical information is also provided to a purchaser of the product produced by the invention. The numerical information described herein or portions thereof may be stored electronically in computer readable format.

The purchaser of the product for use as a transportation or heating fuel may separate the RIN. As set out above, separation of a RIN from a volume of the product for use as a transportation or heating fuel, means termination of the assignment of the RIN to a volume of fuel. RIN separation is typically carried out by a fuel blender, importer or other obligated party. According to pre-2010 regulations, when a RIN is separated, the K code of the RIN is changed to 2.

Separation of RINs may be conducted in accordance with prevailing rules and regulations, as currently provided in 40 C.F.R. §80.1129 and 40 C.F.R. §80.1429. RINs generated in accordance with the invention may be separated and subsequently traded.

It should be understood that the regulations under EISA, including RIN requirements and the criteria for categorization of a fuel under a particular fuel category, such as life cycle GHG emission thresholds, are described herein in accordance with current regulations and that the invention is not limited to current rules and will provide benefits in relation to subsequent rule changes thereof.

(b) Low Carbon Fuel Standard (LCFS)

The beneficial GHG emissions reductions achieved by the present invention can provide a means for meeting low carbon fuel standards established by jurisdictions within the United States or other government authorities. The credit, which includes a certificate, may be associated with one or more products from the process, and represents or is proportional to the amount of life cycle GHG emissions reduced measured relative to a gasoline baseline. As set forth previously, the life cycle GHG emissions under low carbon fuel standards are often referred to as carbon intensity or CI.

California's LCFS currently requires that all mixes of fuel that oil refineries and distributors sell in the Californian market meet in aggregate the established targets for GHG emissions reductions. California's LCFS requires increasing annual reductions in the average life cycle emissions of most transportation fuels, up to a reduction of at least 10% in the carbon intensity, which is a measure of the life cycle GHG emissions, by 2020. Targets can be met by trading of credits generated from the use of fuels with a lower GHG emission value than gasoline baseline. Similar legislation has been implemented by the province of British Columbia, Canada, the United Kingdom and by the European Union.

According to some embodiments of the invention, LCFS fuel credit generation comprises generating information associated with the one or more products produced by the process of the invention for use as a transportation or heating fuel. A party may generate information relating to at least one parameter selected from (i) a reporting period; (ii) a fuel pathway code; (iii) transaction information, including type or date of a transaction; (iv) fuel production facility information; (v) fuel delivery methods; (vi) an amount of fuel used as a fossil fuel replacement, such as gasoline or diesel; and (vii) credits or deficits generated. In a further embodiment, information regarding at least two parameters, at least three parameters or at least four parameters is generated from the foregoing list.

British Columbia, Canada, approved a Renewable and Low Carbon Fuel Requirements Act, which requires parties who manufacture or import the fuel into the province ensure that the renewable content and the average carbon intensity of the fuel they supply meets levels set by regulations. Fuel suppliers are required to submit annual reports regarding the renewable fuel content and carbon intensity of the transportation fuels they supply. The province allows transfers of GHG credits between fuel suppliers to provide flexibility in meeting the requirements of the regulation.

In the European Union, GHG emissions are regulated by a Fuel Quality Directive, 98/70/EC. In April 2009, Directive 2009/30/EC was adopted which revises the Fuel Quality Directive 98/70/EC. The revisions include a new element of legislation under Article 7a that requires fuel suppliers to reduce the GHG intensity of energy supplied for road transport (Low Carbon Fuel Standard). In particular, Article 7a specifies that this reduction should amount to at least 6% by 31 Dec. 2020, compared to the EU-average level of life cycle GHG emissions per unit of energy from fossil fuels in 2010. According to the Fuel Quality Directive, fuel/energy suppliers designated by member states of the European Union are required to report to designated authorities on: (a) the total volume of each type of fuel/energy supplied, indicating where the fuel/energy was purchased and its origin; and (b) the life cycle GHG emissions per unit of energy. The European Union has also promoted the use of biofuels through a Biofuel Directive (2003/30/EC), which mandates countries across the EU to displace certain percentages of transportation fuel with biofuels by target dates.

The United Kingdom has a Renewable Transport Fuel Obligation in which biofuel suppliers are required to report on the level of carbon savings and sustainability of the biofuels they supplied in order to receive Renewable Transport Fuel Certificates (RTFCs). Suppliers report on both the net GHG savings and the sustainability of the biofuels they supply according to the appropriate sustainability standards of the feedstocks from which they are produced and any potential indirect impacts of biofuel production, such as indirect land-use change or changes to food and other commodity prices that are beyond the control of individual suppliers. Suppliers that do not submit a report will not be eligible for RTFCs.

Certificates can be claimed when renewable fuels are supplied and fuel duty is paid on them. At the end of the obligation period, these certificates may be redeemed to the RTFO Administrator to demonstrate compliance. Certificates can be traded. Therefore, if obligated suppliers do not have enough certificates at the end of an obligation period they have to 'buy-out' the balance of their obligation by paying a buy-out price.

EXAMPLES

Example 1

This example demonstrates that processing wheat straw to remove extractives can improve its heating value relative to untreated wheat straw and lignite coal.

The heating value (Btu/lb) of three samples was tested in gasification, namely untreated wheat straw, acid pretreated wheat straw and dried lignin. The samples were prepared as follows:

(i) Wheat straw: the feedstock was subjected to a size reduction to produce particles of a size between 2 and 4 inches in length by shredding.

(ii) Pretreated wheat straw: Size reduced wheat straw having a particle size between 2 and 4 inches in length was soaked with sulfuric acid at a pH of 1.4. The acid soaked feedstock was dewatered in a screw press and subsequently pretreated as described in U.S. Publication No. 2013/0071903, which is incorporated herein by reference in its entirety. After acid pretreatment, the pretreated fiber solids were washed with water and neutralized with ammonium hydroxide to achieve a pH of about 5.

(iii) Dried lignin: The lignin sample was obtained by pretreating wheat straw with sulfuric acid at pH 1.4 as described above. The pretreated feedstock was pH adjusted to a value of about 5 with alkali to produce a neutralized, pretreated feedstock slurry. The cellulose in the slurry was hydrolyzed with cellulase enzymes secreted by a strain of *Trichoderma reesei* to produce a hydrolyzed slurry comprising glucose. After enzymatic hydrolysis, lignin and other insoluble components were removed from the hydrolyzed slurry by a filter press. The lignin was subsequently dried to remove liquid.

The gross calorific value, also referred to as the high heating value, of unprocessed wheat straw, acid pretreated wheat straw and lignin obtained from the wheat straw, prepared as described above, was determined by loading a lab scale fixed-bed gasification reactor with the samples. The reactor was loaded with 27 to 240 grams of sample, depending on the bulk density of the sample. The reactor was heated to a final temperature of 750-800° C. The reactor was held at this temperature until gas production was minimal. At that time, the heaters were shut off and opened to facilitate rapid temperature reduction of the reactor. The heating values were determined using ASTM D2015-96).

The heating values for each sample are presented in Table 3 below.

TABLE 3

High heating values of lignite coal, lignin from untreated wheat straw, pretreated wheat straw

| Lignite A coal | Untreated wheat straw | Pretreated wheat straw | Lignin |
|---|---|---|---|
| 6300-8300 Btu/lb* | 7,035 Btu/lb | 7,887 Btu/lb | 8,589 Btu/lb |

*Value obtained from Bell et al., "Chapter 1 - The Nature of Coal". *Coal Gasification and its Applications* (Oxford: William Andrew, 2011).

The gross calorific value was the highest for lignin, followed by the pretreated wheat straw and untreated wheat straw. The lignin also possessed a heating value that was significantly higher than Lignite A coal.

The foregoing results were obtained on material that was not densified. Densification can be utilized to further improve the energy value of the processed biomass feedstock fed to the gasification reactor as the energy per volume (Btu/ft$^3$) can be significantly improved. In the case of the lignin and the pretreated wheat straw, after densification, the energy per volume would be higher than lignite A coal. As a result, more energy per volume may be gasified in the gasification reactor. Thus, co-gasifying coal and processed biomass feedstock could potentially improve the efficiency of the process over processing lignite coal alone.

The present invention has been described with regard to one or more embodiments. However, it will be apparent to those of skill in the art that a number of variations and modifications can be made without departing from the scope of the invention as defined in the claims.

What is claimed is:

1. A process for producing a fuel and a byproduct from biomass or biomass derived material, said process comprising the steps of:
   (i) providing a processed biomass feedstock for use in gasification;
   (ii) carrying out or causing one or more parties to carry out a gasification process comprising:
      (a) subjecting the processed biomass feedstock to gasification to produce a product comprising carbon monoxide and hydrogen and cresylic acid, wherein the processed biomass feedstock is co-gasified with coal, and wherein the gasification is conducted in at least one Lurgi-type bed reactor;
      (b) recovering at least a portion of the cresylic acid and providing a chemical product comprising the recovered cresylic acid;
      (c) recovering the hydrogen produced or derived from step (ii)(a) or further reacting the carbon monoxide and hydrogen to produce a fuel or fuel intermediate;
      (d) providing one or more products obtained from step ii(c), for use as, or to produce a transportation or heating fuel; and
      (e) generating or causing generation of a renewable fuel credit.

2. A process for producing a fuel and a byproduct from biomass or biomass derived material comprising the steps of:
   (i) providing a processed biomass feedstock resulting from at least one extractive releasing processing step;
   (ii) carrying out or causing one or more parties to carry out a gasification process comprising:
      (a) subjecting the processed biomass feedstock to gasification to produce carbon monoxide and hydrogen and cresylic acid, said gasification conducted in at least one Lurgi-type reactor;
      (b) recovering at least a portion of the cresylic acid and providing a chemical product comprising the recovered cresylic acid;
      (c) recovering the hydrogen produced or derived from step (ii)(a) or further reacting the carbon monoxide and hydrogen to produce a fuel or fuel intermediate;
      (d) providing one or more products obtained from step (ii)(c), for use as, or to produce a transportation or heating fuel; and
      (e) generating or causing generation of a renewable fuel credit.

3. A process for producing a fuel and a byproduct from biomass or biomass derived material comprising the steps of:
   (i) providing a processed biomass feedstock that is densified;
   (ii) carrying out or causing one or more parties to carry out a gasification process comprising:
      (a) subjecting the processed biomass feedstock of step (i) to gasification to produce carbon monoxide and hydrogen and cresylic acid, said gasification conducted in at least one Lurgi-type reactor;
      (b) recovering at least a portion of the cresylic acid and providing a chemical product comprising the recovered cresylic acid;
      (c) recovering the hydrogen produced or derived from step (ii)(a) or further reacting the carbon monoxide and hydrogen to produce a fuel or fuel intermediate;
      (d) providing one or more products obtained from step (ii)(c), for use as, or to produce a transportation or heating fuel; and
      (e) generating or causing generation of a renewable fuel credit.

4. A process for producing a fuel and a byproduct from biomass or biomass derived material, said process comprising the steps of:
   (i) subjecting a processed biomass feedstock to gasification to produce a product comprising carbon monoxide and hydrogen and cresylic acid, wherein the processed biomass feedstock is co-gasified with coal, and wherein the gasification is conducted in at least one Lurgi-type reactor;

(ii) recovering at least a portion of the cresylic acid and providing a chemical product comprising the recovered cresylic acid;

(iii) recovering the hydrogen produced or derived from step (i) or further reacting or causing one or more parties to further react the carbon monoxide and hydrogen to produce a fuel or fuel intermediate;

(iv) providing one or more products obtained from step (iii), for use as, or to produce a transportation or heating fuel; and (v) generating or causing generation of a renewable fuel credit.

5. A process for producing a fuel and a byproduct from biomass or biomass derived material comprising the steps of:

(i) subjecting a processed biomass feedstock resulting from at least one extractive releasing process step to gasification to produce carbon monoxide and hydrogen and cresylic acid, said gasification conducted in at least one Lurgi-type reactor;

(ii) recovering at least a portion of the cresylic acid and providing a chemical product comprising the recovered cresylic acid;

(iii) recovering the hydrogen produced or derived from step (i) or further reacting or causing one or more parties to further react the carbon monoxide and hydrogen to produce a fuel or fuel intermediate;

(iv) providing one or more products obtained from step (iii), for use as, or to produce a transportation or heating fuel; and (v) generating or causing generation of a renewable fuel credit.

6. A process for producing a fuel and a byproduct from biomass or biomass derived material comprising the steps of:

(i) receiving a processed biomass feedstock that is densified;

(ii) subjecting the processed biomass feedstock that is densified to gasification to produce carbon monoxide and hydrogen and cresylic acid, said gasification conducted in at least one Lurgi-type bed reactor;

(iii) recovering at least a portion of the cresylic acid and providing a chemical product comprising the recovered cresylic acid;

(iv) recovering the hydrogen produced or derived from step (ii) or further reacting or causing one or more parties to further react the carbon monoxide and hydrogen to produce a fuel or fuel intermediate;

(v) providing one or more products obtained from step (iv), for use as, or to produce a transportation or heating fuel; and (vi) generating or causing generation of a renewable fuel credit.

7. The process of claim 6, wherein the fuel or fuel intermediate is methane.

8. The process of claim 6, wherein the biomass is straw, stover or an energy crop.

9. The process of claim 6, wherein the cresylic acid comprises o-cresol, m-cresol or p-cresol.

10. The process of claim 6, wherein the processed biomass feedstock is size reduced.

11. The process of claim 6, wherein 90% of the processed biomass feedstock by weight has a particle size that is between ¼ inch and 6 inches in diameter.

12. The process of claim 11, wherein 90% of the processed biomass by weight has a particle size that is between ⅜ inch and 4 inches in diameter.

13. The process of claim 2, wherein the extractive releasing processing step removes at least a portion of hemicellulose from a biomass or biomass derived material.

14. The process of claim 6, further comprising recovering phenols.

15. The process of claim 6, wherein the processed biomass feedstock contains greater than 40 wt % lignin (w/w).

16. The process of claim 6, wherein less than 10 wt % of the ash in the processed biomass feedstock is potassium (w/w).

17. The process of claim 6, wherein the transportation fuel or fuel intermediate is methane.

18. The process of claim 6, wherein the processed biomass feedstock has an amount of potassium removed therefrom and the ash fusion temperature of ash formed during gasification is at least 5° C. higher than the operating temperature of the gasification.

19. The process of claim 6, wherein the processed biomass feedstock has a cellulose content of 0 to 50% (w/w).

20. The process of claim 6, wherein the processed biomass feedstock comprises lignin recovered after an enzymatic hydrolysis.

21. The process of claim 6, wherein the processed biomass feedstock comprises biomass pretreated with acid.

* * * * *